US011154190B2

(12) United States Patent
Kessels et al.

(10) Patent No.: US 11,154,190 B2
(45) Date of Patent: Oct. 26, 2021

(54) EYE SURFACE TOPOGRAPHER

(71) Applicant: Eaglet Eye B.V., Houten (NL)

(72) Inventors: Henricus M. M. Kessels, Weert (NL);
Jan G. M. Brassé, Roermond (NL);
Christiaan H. F. Velzel, Deurne (NL)

(73) Assignee: Eaglet Eye B.V., Houten (NL)

( * ) Notice: Subject to any disclaimer, the term of this patent is extended or adjusted under 35 U.S.C. 154(b) by 426 days.

(21) Appl. No.: 16/071,248

(22) PCT Filed: Jan. 20, 2017

(86) PCT No.: PCT/EP2017/051144
§ 371 (c)(1),
(2) Date: Jul. 19, 2018

(87) PCT Pub. No.: WO2017/125528
PCT Pub. Date: Jul. 27, 2017

(65) Prior Publication Data
US 2020/0138286 A1 May 7, 2020

(30) Foreign Application Priority Data

Jan. 20, 2016 (EP) .................................. 16152075
Mar. 18, 2016 (EP) .................................. 16161200

(51) Int. Cl.
*A61B 3/107* (2006.01)
*A61B 3/14* (2006.01)
(Continued)

(52) U.S. Cl.
CPC .............. *A61B 3/107* (2013.01); *A61B 3/145* (2013.01); *G01B 11/255* (2013.01); *G01B 11/2536* (2013.01)

(58) Field of Classification Search
CPC .......... A61B 3/107; A61B 3/14; A61B 3/145; G01B 11/2536; G01B 11/255; G01B 11/25
See application file for complete search history.

(56) References Cited

U.S. PATENT DOCUMENTS

| 5,406,432 A | 4/1995 | Murray |
| 2008/0018856 A1 | 1/2008 | Sarver et al. |

FOREIGN PATENT DOCUMENTS

EP   0551955 B1   8/1997

OTHER PUBLICATIONS

Jongsma et al., "A Moiré based corneal topographer suitable for discrete Fourier analysis", SPIE, vol. 2126, Opthalmic Technologies IV, 1994 pp. 185-192.

(Continued)

*Primary Examiner* — Jack Dinh
(74) *Attorney, Agent, or Firm* — Dinsmore & Shohl, LLP

(57) ABSTRACT

The invention concerns a system for determining the topography of a diffusely reflecting curved surface, that comprises two telecentric projection branches that project fringe images of a Ronchi grating on the diffusely reflecting curved surface, and a viewing branch of which the optical system projects an image of the illuminated surface on its camera target, and comprises further a computer that receives the fringe images recorded by the camera target and calculates from these the topography of the anterior eye surfaces, in which system the projection sources are semiconductor diodes and the optical system of the viewing branch is two-sided telecentric.

13 Claims, 2 Drawing Sheets

(51) Int. Cl.
    *G01B 11/255* (2006.01)
    *G01B 11/25* (2006.01)

(56) References Cited

OTHER PUBLICATIONS

Takeda et al., "Fourier-transform method of fringe-pattern analysis for computer-based topography and interferometry", Optical Society of America, vol. 72, No. 1, 1982, pp. 156-160.
International Search Report and Written Opinion, dated Apr. 24, 2017, pertaining to PCT/EP2017/051144, filed Jan. 20, 2017.

EYE SURFACE TOPOGRAPHER

FIELD OF THE INVENTION

The invention relates to an optical system for determining the topography of diffusely curved surfaces. In particular, the present invention relates to an optical system for determining the topography of the front surfaces, cornea and sclera, of the human eye. Said system consists of two fringe projectors that project line patterns on an eye and a camera system that makes images of these fringe patterns, from which images the topography of the front surfaces of the eye can be calculated using specialized software.

BACKGROUND TO THE INVENTION

Classical instruments for measuring parameters of the topography of the cornea are known as keratometers. A significant improvement of the classical keratometer gave rise to the Placido disk corneal topographer that could be used to map a significant portion of the cornea (9 mm horizontally and 7.5 mm vertically). Further improvements of the Placido disk topographer have led to an extension of the measured area to about 11 mm horizontally and 10 mm vertically. The Placido disk does not measure the height of the cornea directly, but because it uses the reflective properties of the cornea it is sensitive mainly to the slope of the cornea. This ensures an accurate measurement of corneal curvatures except in the central part of the cornea. When the corneal surface is not spherical, however, the measurement by the Placido disk topographer is less accurate.

Moreover the measurement area of the Placido instrument is limited to the cornea because of its reflective properties. Measurement of the scleral surface, that has more different optical properties, is not possible with the Placido topographer.

The wish to extend the measurement of the front surfaces of the eye to the sclera led to a number of systems that used principles different from that of the reflection-based Placido disk topographer. Predecessors of the system according to the present invention use raster photogrammetry, slit projection or fringe projection. The system according to the present invention is based on fringe projection. The Maastricht Surface Topographer (MST) described in EP 0551955 B1 is its immediate predecessor. The MST promised a wide field (20 mm) height image of cornea as well as sclera, but due to insufficient computing power it was never introduced in the market.

SUMMARY OF THE INVENTION

It is an object of the present invention to provide a new system for determining the topography of a diffusely reflecting curved surface. More in particular, the present invention relates to an optical system for determining the topography of the front surfaces, cornea and sclera of the human eye, hereinafter also referred to as an Eye Surface Topographer (EST).

The system for determining the topography of a diffusely reflecting curved surface according to the present invention comprises two telecentric projection branches that independently project fringe images of a Ronchi grating on the diffusely reflecting curved surface, a viewing branch of which the optical system projects an image of the diffusely reflecting curved surface on its camera target, and a computer that receives the fringe images recorded by the camera target and calculates the topography of the diffusely reflecting curved surface. Said system is characterized in:

that the projection sources in the projection branches are semiconductor diodes that send out light of a wavelength between 400 and 500 nm;

that the optical axes of the projection branches and the viewing branch lie in one plane;

that the angles between the axes of the projection branches and the viewing branch are equal and opposite, and that the three axes intersect in one point;

that the optical system of the viewing branch is telecentric in its object space and its image space and transmits light of wavelength longer than 500 nm; and that a focusing tool is included in the system, said focusing tool comprising two narrow beams (15) and (16) focused from different angles on the surface to be measured.

As indicated above, the system according to the present invention comprises two telecentric projection branches. Said projection branches each comprise a fringe projector that comprises the following components listed according to the propagation direction of the light: a semiconductor diode (1) that emits radiation with a wavelength around a central value smaller than for example 500 nm, a filter glass (2) that transmits no radiation of a wavelength longer than said wavelength, a condenser lens (3), a Ronchi grating (4) mounted in a fitting that can rotate the grating around the optical axis over small angles with a high accuracy, a slit diaphragm (5) that selects the lowest diffraction orders of the Ronchi grating, and a projection lens (6) that projects filtered images of the Ronchi grating on the projection plane (7). It is preferred that during measurement the diffusely reflecting curved surface, in particular the anterior eye surface of the test person, touches said projection plane (7). Also in the system, the slit diaphragm (5) in the projection branch has its axial position in the front focal plane of the projection lens (6) so that the projection is telecentric.

In a particular embodiment of the present invention, the semiconductor diodes (1) are light emitting diodes. In another particular embodiment of the present invention, the semiconductor diodes (1) are blue diode lasers.

As indicated above, typical for the present invention is that the angles between the axes of the projection branches and the viewing branch are equal and opposite, and that the three axes intersect in one point. In a particular embodiment, the optical axes of the projection branches make angles from 10° to 45° with the projection plane (7).

The system according to the present invention also comprises a viewing branch. Said viewing branch comprises two lens groups that have a common focal point in which point the aperture stop (10) is situated, so that the optical system of the viewing branch is double-sided telecentric. The viewing branch further comprises a camera target (13), a camera lens (12), a glass filter (11), a diaphragm (10) and a front lens (9). The camera target (13) (for example a CCD-target) is situated in the back focal plane of the rear group. During measurement, the system must be brought in focus so that the diffusely reflecting curved surface, in particular the eye front surface of the test person, is near the front focal plane of the front lens group (9). In the viewing branch of the system according to the present invention, a glass filter is placed near the diaphragm of the aperture stop. Said glass filter (11) transmits only radiation with a wavelength longer than, for example, 500 nm.

Also typical for the present invention is that a focusing tool is included in the system. Said focusing tool comprises two narrow beams (15) and (16) focussed from different angles on the surface to be measured. Said narrow beams come from positions from the side of the front lens (9) in the viewing branch and have a wavelength in the near infrared (for example 800 nm). The operator judges the position of focus from the sideways distance of the spots on the curved surface, for example the cornea. The correct focus is obtained when this distance is equal to zero.

The images recorded by the camera target (13) are sent to the processing system. The processing software calculates the height difference between the anterior eye surfaces and a plane through the top of the cornea perpendicular to the optical axis of the camera system. The object field of the camera system and the fields of the two projectors must have a sufficient diameter to chart the whole visible part of the anterior eye surface (with the eye-lids folded aside, if necessary). With the system according to the present invention a field diameter of 25 mm can be offered.

During measurement of the anterior eye surfaces, drops of a solution of Na-fluorescine or any solution acceptable to the eye are added to the tear layer of the eye so that the eye front surfaces become diffusely reflecting objects. The method of fringe projection at an angle on which the present system is based makes this necessary. Addition of fluorescine in the tear layer is an established technique in optometry. The fluorescine emits yellow-green light on excitation with blue light. After application of the fluorescine, a measurement of the eye topography can be performed. The optical system is first focused on the cornea of the eye to be measured with the aid of a focusing tool that we will describe below. Next, short exposures of the fringe patterns are made by the two projection LED's successively. The exposure times and the time interval between the two exposures must be so small that involuntary eye movements are negligible (milliseconds).

In comparison with the preceding MST system, as described in the patent EP 0551955 B1, the system according to the present invention has been improved in several ways that we describe in the following.

In the MST system the projection sources were flash lamps, whereas we use semiconductor diodes, for example light emitting diodes (LED) or blue diode lasers. Whereas a flash lamp has a broad spectrum in the whole visible range and beyond, LED's have spectra with a spectral width of, for example, 50 nm, so that a LED with a wavelength of 475 nm has very little power above 500 nm. Therefore it is easy, with a LED, to separate the excitation radiation from the fluorescence, whereas with a flash light it is more difficult and requires expensive filters.

To still further improve the spectral discrimination, it is possible to use blue diode lasers instead of the LED's.

In the MST system a ready-made camera was used (see patent EP 0551955 B1) so that the telecentricity of the camera system was not perfect on the image side and vignetting could occur and could cause shading in the image intensity distribution and lead to systematic errors in the measurement results. The camera system of the EST system according to the present invention is double-sided telecentric and free of vignetting. This makes that focus errors (defocus, target tilt, astigmatism and field curvature) lead to a loss of contrast in the recorded fringe pattern, but do not cause fringe shifts that lead to topography errors. In the MST system as described in EP0551955 B1, focusing was controlled by the operator by inspection of the camera images.

Another difference with the MST system is the presence of a focusing tool in the system. Said focusing tool comprises two narrow beams (15) and (16) focussed from different angles on the surface to be measured. Per reference to FIG. 2, using such narrow beams coming from the side and within the viewing branch of the front lens (9), an out-of-focus position is evident from sharp small and readily identifiable spots sideways from the central position. Being sharp and well delineated spots, focussing is made easy and achieved when these spots merge, i.e. when the distance between the spots is equal to zero.

In another embodiment of the present invention, the focus criterion is obtained in an automated manner by the computer software, making the focusing more accurate. Accurate focusing is important because higher order errors in the object-side telecentricity can lead to topography errors; when the focusing is more accurate (or when the defocus distance is known more accurately) it is possible to correct these topography errors by a software code.

In yet another embodiment, the optical system is moved by a servomotor controlled by the computer (14), thereby automating the focusing.

For an accurate measurement of the topography of the diffusely reflecting curved surface the following requirements must be met by the optical system.

The fringe patterns in a plane perpendicular to the camera optical axis must consist of straight lines and have a uniform period that is the same for both projections and independent of defocusing over a distance of, for example, 5 mm. This can be achieved by fine-tuning the magnification of the projection lenses (6), provided that the aberrations of these lenses are sufficiently well corrected. The fine-tuning is done by hand during the assembling of the system by small axial displacements of the lenses and measurement of the fringe period by computer software. Preferably, in the system according to the present invention the projection lenses (6) can be moved axially by actuators; in particular with the aid of computer calculations of the fringe images in the projected fringe images. In this manner, the telecentricity of the projection branches is improved.

The orientation of the fringes in the projection plane (7) must be perpendicular to the plane formed by the projection axes. In a particular system according to the invention this can be done by rotation of the Ronchi gratings. Thus, in a particular embodiment of the present invention, the orientation of the Ronchi gratings (4) can be controlled by rotating said gratings by actuators. In a preferred embodiment controlling of the orientation of the Ronchi gratings (4) by the operator is done with the aid of computer calculations of the orientation of the projected fringe patterns. In an even further embodiment the orientation of the Ronchi gratings (4) is monitored by the computer. A condition for this operation is that during assembling the optical axes of the projection branches and the viewing branch are brought in one plane perpendicular to the column direction of the camera target and that the angles between the projection axes and the viewing axis are made equal and opposite, for example ±20°. This is made possible in the EST optical system by folding the optical path of the projection branches by two mirrors on equal but opposite distances from the slit diaphragm. Thus, in a particular embodiment of the present invention, the optical axis of one or both, in particular of both of the projection branches is folded by two mirrors positioned on equal but opposite distances from the slit diaphragm (5). In a further embodiment, said mirrors are rotatable over small angles about their nominal position and about perpendicular rotations axes. As a result, degrees of freedom are created, together with the coordinate of the LED's and sideways shifts of the slit, sufficient for this operation. In an even further embodiment, an infrared light emitting diode (LED) can be mounted behind one of the mirrors. This LED is aimed for making photographs of the eye before and after the measurement. In a particular embodiment, the mirror has a dichroic beamsplitter coating.

For comparing the results of the EST measurement with other measurements of Eye Surface Topography or with other optometric measurements such as Placido keratometry it is important that the visual axis of the eye is directed along the optical axis of the viewing branch during the EST measurement. For this purpose a back-illuminated object is virtually imaged with its center on said optical axis by a beam splitter mirror and the test person is asked to fixate this object during the measurement. Thus, in a particular embodiment of the present invention, a backlighted object (20) is mounted in the optical system of the viewing branch that is imaged by a beam splitting mirror (21) on the aperture stop (10).

The processing of the images recorded by the camera target of the viewing branch is essential in obtaining the topography of the anterior eye surface in the form of a height image. The algorithm used in EST is an extension of the algorithm published by Takeda (J. Opt. Soc. Am. 1982; 72(1); 156-160). This algorithm has been adapted to the requirements of the present EST system. The main adaptations are: measurement of small differences in fringe frequency and orientation in the two projection branches; pre-processing and masking in the two images; matching and combining of the two height images made with the two projectors into a final height image.

The final height image can be used to obtain parameters that are useful in ophthalmological applications.

This makes a comparison possible with other methods of corneal topography, such as Placido videokeratoscopy. In a particular embodiment, the system according to the present invention is for use as a keratometer. In particular, the present invention also discloses the use of a system according to the present invention as a keratometer.

In a further embodiment, the present system is for use in eye care applications. Therefore, also the use of the present system in eye care applications is disclosed; Even more in particular, such eye care applications are selected from the group comprising, but not limited to, contact lens fitting or eye imaging during surgery. After all, because EST obtains topographical data of the sclera as well, the fitting of contact lenses that use the sclera as a support can be improved. The data of the EST height image can be used as input in a computer program for the design of contact lenses. Therefore, the system according to the present invention is for use as a contact lens fitting device. The present invention therefore also discloses the use of the system according to the invention as contact lens fitting device.

The EST system in its present state has been validated by measurements of the surface of curved objects, consisting of fluorescent materials. The measurement accuracy in a central region of the cornea with a diameter of 10 mm and a radius of curvature of 8 mm, so that the sagitta was 1.5625 mm, was found to be ±0.002 mm. In a peripheral region with diameters between 10 and 20 mm and a radius of curvature of 12 mm so that the sagitta increased with 3.125 mm, the measurement accuracy was ±0.010 mm.

Some unique features of the anterior eye that can be quantified by the EST system are: the topography of the limbus and the position of the apex of the cornea, the asymmetries of the cornea and the toricity of the sclera surface. Thus, in a particular embodiment, the system according to the present invention is for use as a topographer of the limbus and the sclera of the human eye. The present invention also discloses the use of a system according to the present invention as a topographer of the limbus and the sclera of the human eye.

The limbus forms the transition between the transparent cornea and the translucent sclera. Its radial range lies between 12 and 14 mm. The topography of the limbus cannot be obtained by Placido disk videokeratoscopy; though it can be obtained by EST with an accuracy of ±0.005 mm. This is an important item in the fitting of contact lenses. The topography of the limbus can also be used to determine the position of the apex of the cornea.

Asymmetries of the cornea, mainly occurring along a horizontal cross-section (nasal to temporal) can be quantified accurately using EST. This is possible because of the extended measuring range of EST.

From EST measurements it turns out that the sclera has a weakly toroidal form, different on the nasal and temporal sides of the eye. This again is an important feature in contact lens fitting.

In a further embodiment, the EST system according to the present invention can also be used in capturing high-quality images of the eye. Capturing high-quality images of the eye has been a challenge in computer graphics for years already, and eye models typically used are currently insufficient for capturing the individual identity of the human eye. After all, the complexity of the human eye requests a specific approach for capture and accurate reconstruction. Due to its technical specifications and its accurate measurement capacity, as outlined above, the present EST system is also for use in capturing high-quality images of the eye. In another embodiment, the present EST system is for use in high-quality image reconstruction of the eye. Therefore, the present invention also discloses the use of the present system in capturing high-quality images of the eye or in high-quality image reconstruction of the eye.

Both image capturing as well as image reconstruction are crucial for a veracious image reconstruction of the eye, for example in virtual reality applications, such as computer graphics. Therefore, in yet another embodiment, the EST system according to the present invention is for use in virtual reality applications, such as for example video games, film industry, training and simulation, or behavioural training. The presently available imaging technologies for capturing high-quality images of the eye are time consuming (45 minutes or more) and generally request a specific horizontal position of the test person, eventually including a horizontal fixation of the test person's head. With the present EST system, capturing of high-quality images of the eye can be performed in only a few minutes, thereby reducing the costs and increasing the comfort of the test person. Furthermore, the easy handling of the EST system allows the system to be used on a person, simply sitting or standing in an upright position, thereby additionally improving the comfort of the test person. Thus, in a further embodiment, the use of the system according to the present invention in virtual reality applications is disclosed.

High-quality images of the eye are defined as virtual eyes that are beyond "the uncanny valley". The uncanny valley is a hypothesis in the field of aesthetics, which holds that when features look and move almost, but not exactly, like natural beings, it causes revulsion among some observers. The "valley" refers to the negative dip in emotional response right before the point at which something looks and acts fully human. The uncanny problem shows up when synthetic representation of humans (e.g. avatars) act enough like humans to generate expectations of normal human appearance or behaviour, but then frustrate these expectations, thus causing a feeling of strangeness of lack of comfort on the part of the real human users of the system. Thus improved methods of controlling avatars that are beyond said uncanny valley would be desirable and useful, because such methods would facilitate online computer assisted communications among various human users.

In yet another embodiment of the present invention, the system according to the present invention is for motion capture of the human eye. Motion capture is the process recording the movement of object or people. In the present invention, the EST system is for use of motion capture of the human eye in virtual reality applications, such as for example video games, film industry, training and simulation, or behavioural training. In another embodiment, the present inventions discloses the use of the present system in motion capture of the eye.

In yet another embodiment of the present invention, the system according to the present invention is used in the manufacture of ocular prostheses. In a particular embodiment, the system according to the present invention is used in capturing high-quality images of the eye and in high-quality image reconstruction of the eye, where after these images are used in the manufacture of ocular prostheses. After all, ocular prostheses are also subject to 'the uncanny valley'. With the system according to the present invention, the virtual eyes that are beyond the uncanny valley and that are generated from the high-quality images and after high-quality image reconstruction can be used for the manufacture of ocular prostheses. Ocular prostheses can be manufactured based on the high-quality images that are generated by the system according to the present invention, for example by the use of 3D printing technologies. Thus, in an additional embodiment, the use of the present system in the manufacture of ocular prostheses is disclosed.

BRIEF DESCRIPTION OF THE DRAWINGS

With specific reference now to the figures, it is stressed that the particulars shown are by way of example and for purposes of illustrative discussion of the different embodiments of the present invention only. They are presented in the cause of providing what is believed to be the most useful and readily description of the principles and conceptual aspects of the invention. In this regard no attempt is made to show structural details of the invention in more detail than is necessary for a fundamental understanding of the invention. The description taken with the drawings makes apparent to those skilled in the art how the several forms of the invention may be embodied in practice.

In the drawings, identical elements are labelled with the same reference numbers.

DETAILED DESCRIPTION OF THE INVENTION

The present invention aims to provide a new system for determining the topography of a diffusely reflecting curved surface. More in particular, the present invention relates to an optical system for determining the topography of the front surfaces, cornea and sclera of the human eye. Said optical system is also called the Eye Surface Topographer (EST). The system according to the present invention is here further described in detail based on the presented figures.

Figure 1:
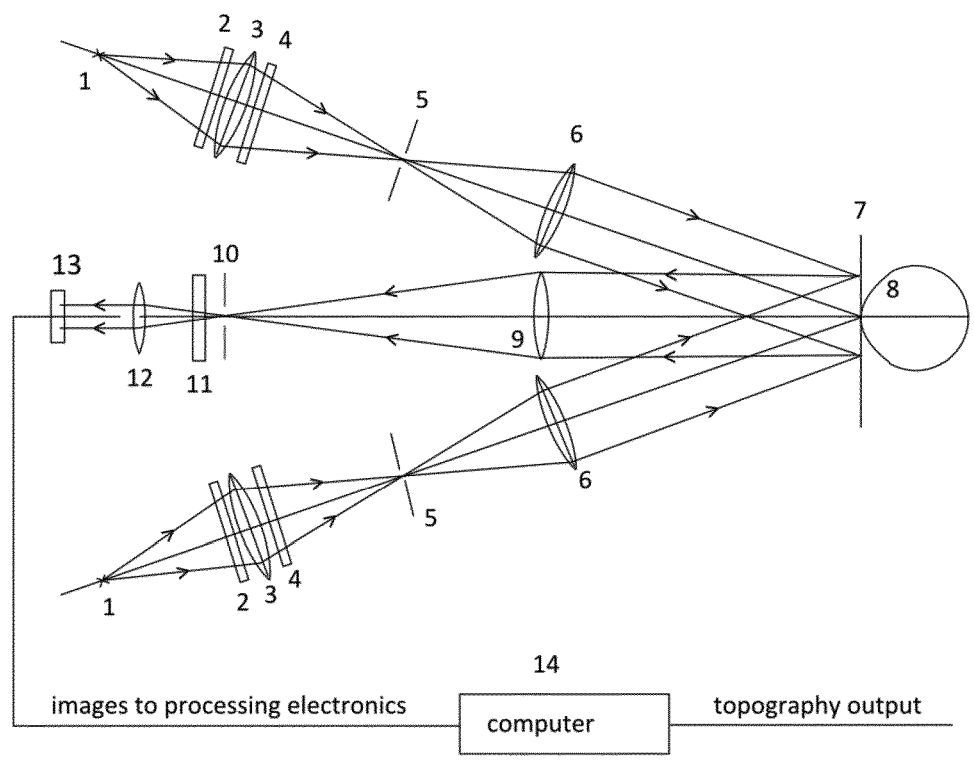
FIG. 1 shows an outline of the EST system in its most elementary form.

FIG. 1 shows an outline of the EST system in its most elementary form. The following components of the EST topographer system can be seen in FIG. 1: (1) is the projection source, which is a semiconductor diode, and thus can be a LED or a blue diode laser, the central wavelength of which is, for example, smaller than 500 nm; the spectral filter (2) blocks all radiation with wavelengths above, for example, 500 nm; the condensor lens (3) projects an image of the source on the slit diaphragm (5); the component (4) is a Ronchi grating that can be rotated in its plane over small angles; the slit diaphragm (5) acts as a spatial frequency filter on the transmission distribution of the Ronchi grating (4); the projection lens (6) projects a sinusoidal intensity distribution with a period of, for example, 250 µm on the plane of projection (7). Because the slit diaphragm (7) is situated in the focal plane of the projection lens (6), the projection is telecentric; on distances of, for example, ±10 mm from the projection plane (7) a useful fringe pattern will be seen. The eye of the test person will be preferably in a position where the top of the anterior eye surface (8) touches the projection plane (7); this can be realized by moving the entire optical system in a direction perpendicular to the projection plane. The viewing branch of the test system according to the present invention consists of the front lens (9), the aperture diaphragm or aperture stop (10), the spectral filter (11) that blocks radiation with wavelengths below, for example, 500 nm, this blocking wavelength being identical to the blocking wavelength of the spectral filter (2); the rear camera lens (12) and the camera target (13). From the camera target the fringe images are sent to the computer (14) that calculate the height image of the anterior eye surface.

Figure 2:
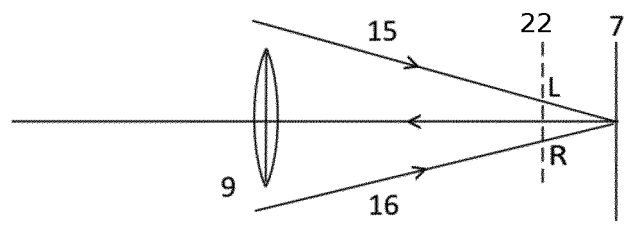
FIG. 2 shows an outline of the focusing tool used in EST.

FIG. 2 shows the principle of the focusing tool used in the EST system according to the present invention. Two narrow beams (15) and (16), coming from positions on the side of the front camera lens (9) (the sources are not shown and can, for instance, be LED's in the focal plane of a lens) are focused in plane (7), on the outer part of the cornea (also not shown). When the cornea is not in the preferred position but with its top in the plane denoted by a dotted line (22), spots are seen by the operator on the computer screen in the positions L and R. Minimizing the sideways distance between the spots gives a perfect focus.

Figure 3:
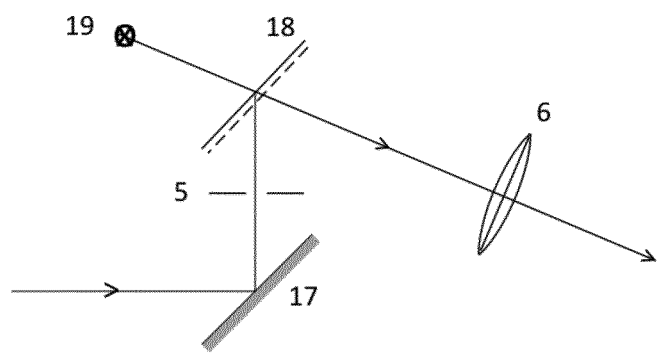
FIG. 3 shows a folded optical path of a projection branch, including an infrared LED for illuminating the eye before and after the blue radiation exposure.

In FIG. 3 a folded version of the projection branch is shown. We recognize the projection lens (6) and the slit diaphragm (5). The mirrors (17) and (18) can be rotated about perpendicular axes over small angles about their nominal positions, the slit diaphragm (5) can be shifted sideways in the plane of the drawing; the mirror (17) can be an aluminium (Al) layer on glass, whereas the beamsplitting mirror (18) is a dichroic dielectric spectral filter. Behind mirror (18) an infrared LED (19) is mounted that illuminates the anterior eye when a photograph is taken by the EST camera.

Figure 4:
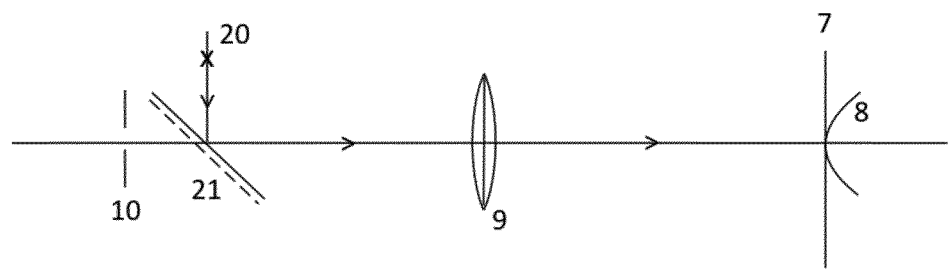
FIG. 4 shows an arrangement for viewing along the visual axis of the eye.

In FIG. 4 a backlighted object (20) is shown that is imaged by the beamsplitter (21) in the plane of the aperture stop (10). During measurement, the test person fixates the object (20) through the camera lens (9) with his eye in position (8) near the plane (7). As a result, the visual axis of the eye is in line with the optical axis of the camera branch during the time of the measurement.

The invention claimed is:
1. A system for determining a topography of a diffusely reflecting curved surface, the system comprising:

two telecentric projection branches that independently project fringe images of a Ronchi grating on the diffusely reflecting curved surface, the two telecentric projection branches each comprising projection sources;

a viewing branch comprising a camera target and an optical system that projects an image of the diffusely reflecting curved surface onto the camera target, the optical system having an object space and an image space;

a focusing tool comprising two narrow beams focused from different angles onto the diffusely reflecting curved surface; and a computer that receives the fringe images recorded by the camera target and calculates the topography of the diffusely reflecting curved surface, wherein:
the projection sources in the two telecentric projection branches are semiconductor diodes that emit light of a wavelength between 400 nm and 500 nm;

each of the two telecentric projection branches has an optical axis, and the viewing branch has an optical axis;

the optical axes of the two telecentric projection branches and the optical axis of the viewing branch all lie in one plane and intersect at one point;

the optical axes of the two telecentric projection branches have equal and opposite angles with the optical axis of the viewing branch; and the optical system of the viewing branch is telecentric in the object space and the image space and transmits light of a wavelength longer than 500 nm.

2. The system according to claim 1, wherein the semiconductor diodes are light emitting diodes (LED).

3. The system according to claim 1, wherein the semiconductor diodes are blue diode lasers.

4. The system according to claim 1, wherein the optical axes of the projection branches make angles from 10° to 45° with a projection plane.

5. The system according to claim 1, wherein a focus criterion is obtained by computer software executable by the computer.

6. The system according to claim 1, wherein the optical system of the viewing branch is moved movable by a servomotor controlled by the computer.

7. The system according to claim 1, wherein the projection branches comprise projection lenses that are axially movable by actuators.

8. The system according to claim 1, wherein an orientation of the Ronchi gratings is controllable by rotating the Ronchi gratings by actuators.

9. The system according to claim 1, wherein one or both of the projection branches comprise two mirrors positioned on equal but opposite distances from the slit diaphragm a slit diaphragm, and wherein the optical axis of each projection branch comprising the two mirrors is folded by the two mirrors.

10. The system according to claim 9, wherein the mirrors are rotatable over small angles about nominal positions of the mirrors and about perpendicular rotation axes of the mirrors.

11. The system according to claim 9, wherein an infrared light emitting diode is mounted behind one of the mirrors.

12. The system according to claim 11, wherein the mirror has a dichroic beamsplitter coating.

13. The system according to claim 1, wherein in the optical system of the viewing branch a backlighted object is mounted that is imaged by a beam splitting mirror on an aperture stop of the viewing branch.

* * * * *